(12) United States Patent
Fresquet

(10) Patent No.: US 9,958,261 B2
(45) Date of Patent: May 1, 2018

(54) DEVICE AND METHOD FOR SURFACE PROFILOMETRY FOR THE CONTROL OF WAFERS DURING PROCESSING

(71) Applicant: FOGALE NANOTECH, Nîmes (FR)

(72) Inventor: Gilles Fresquet, Garrigues-Sainte-Eulalie (FR)

(73) Assignee: UNITY SEMICONDUCTOR, Montbonnot-Saint-Martin (FR)

( * ) Notice: Subject to any disclaimer, the term of this patent is extended or adjusted under 35 U.S.C. 154(b) by 0 days. days.

(21) Appl. No.: 15/513,524

(22) PCT Filed: Sep. 18, 2015

(86) PCT No.: PCT/EP2015/071407
§ 371 (c)(1),
(2) Date: Mar. 22, 2017

(87) PCT Pub. No.: WO2016/046072
PCT Pub. Date: Mar. 31, 2016

(65) Prior Publication Data
US 2017/0299376 A1    Oct. 19, 2017

(30) Foreign Application Priority Data

Sep. 25, 2014   (FR) ..................... 14 59086

(51) Int. Cl.
*G01N 21/00* (2006.01)
*G01B 11/24* (2006.01)
(Continued)

(52) U.S. Cl.
CPC ........ *G01B 11/2441* (2013.01); *G01B 9/0203* (2013.01); *G01B 11/303* (2013.01);
(Continued)

(58) Field of Classification Search
CPC .. G01J 3/02; G01B 9/02; G01B 21/30; G01B 11/2441; G01B 11/303; G01N 21/95; G01N 21/64; G01N 21/68; H01J 37/32935
See application file for complete search history.

(56) References Cited

U.S. PATENT DOCUMENTS

2007/0148792 A1   6/2007   Marx et al.
2013/0038863 A1   2/2013   Fresquet
(Continued)

OTHER PUBLICATIONS

French Search Report from French Patent Application No. 1459086, dated May 13, 2015.
(Continued)

*Primary Examiner* — Abdullahi Nur
(74) *Attorney, Agent, or Firm* — Greer, Burns & Crain, Ltd.

(57) ABSTRACT

A device or apparatus is provided for carrying out measurements of shape on a first surface of a wafer relative to structures present beneath the first surface including (i) profilometry apparatus arranged in order to carry out measurements of shape on the first surface of the wafer according to at least one measurement field; (ii) imaging apparatus facing the profilometry apparatus and arranged in order to acquire a reference image of the structures on or through a second surface of the wafer opposite to the first surface according to at least one imaging field; the profilometry apparatus and said imaging apparatus being arranged so that the measurement and imaging fields are referenced in position within a common frame of reference.
A method is also provided to be implemented in this device or this apparatus.

12 Claims, 2 Drawing Sheets

(51) Int. Cl.
*G01B 11/30* (2006.01)
*G01B 21/30* (2006.01)
*G01B 9/02* (2006.01)
*G01N 21/95* (2006.01)
*G01N 21/88* (2006.01)

(52) U.S. Cl.
CPC ......... *G01B 21/30* (2013.01); *G01N 21/9501* (2013.01); *G01B 2210/56* (2013.01); *G01N 2021/8841* (2013.01)

(56) References Cited

U.S. PATENT DOCUMENTS

2013/0077100 A1* 3/2013 Fukui ................ G01B 11/2441
356/511
2015/0228069 A1 8/2015 Fresquet et al.

OTHER PUBLICATIONS

International Search Report from International Patent Application No. PCT/EP2015/071407, dated Dec. 18, 2015.

* cited by examiner

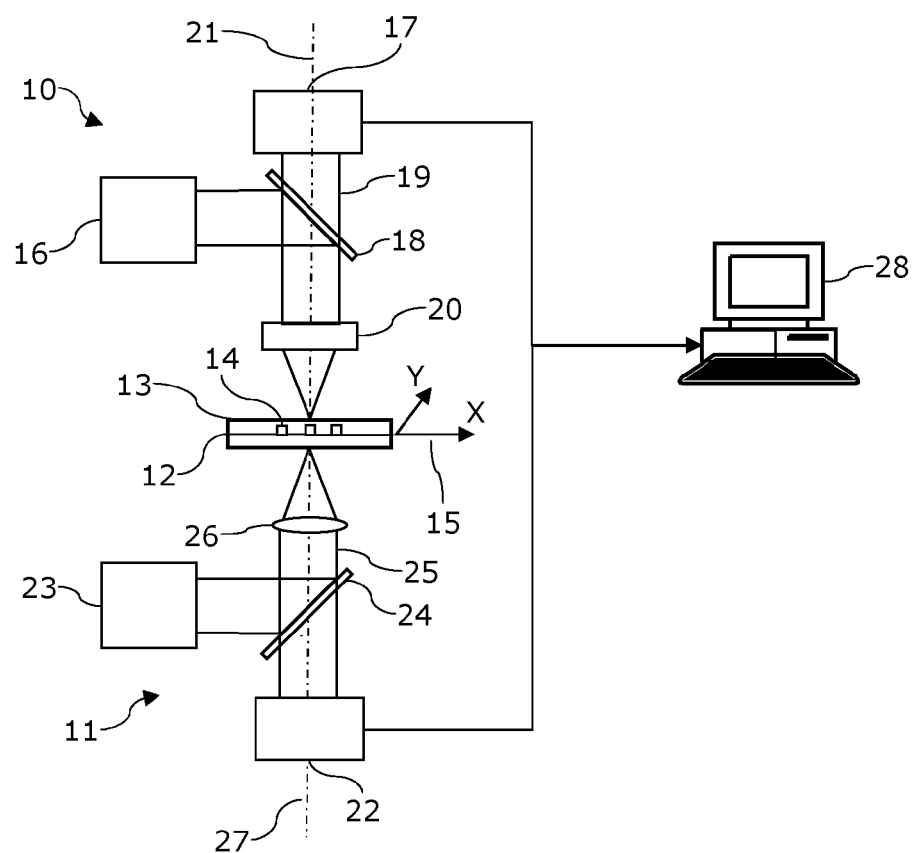
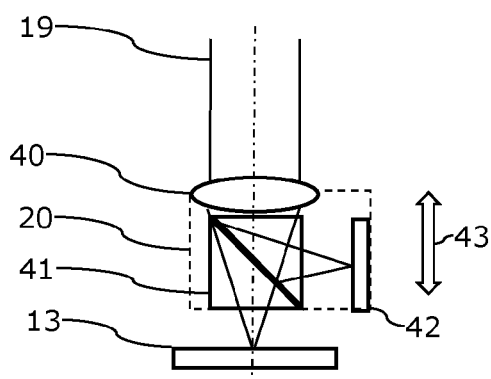
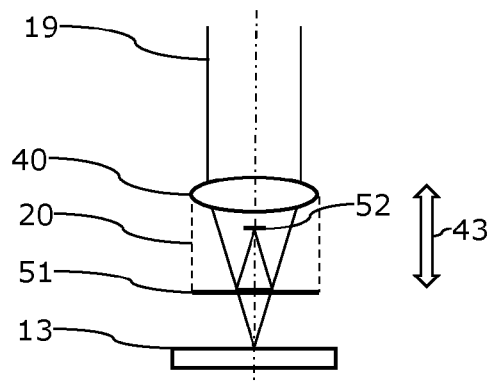
Fig. 1
Fig. 2
Fig. 3

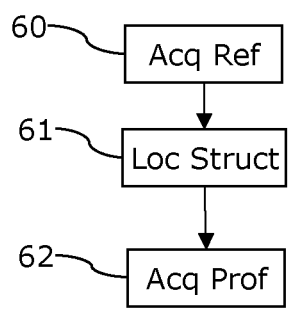
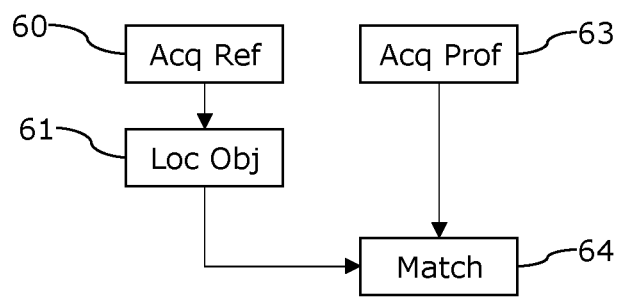
Fig. 4         Fig. 5
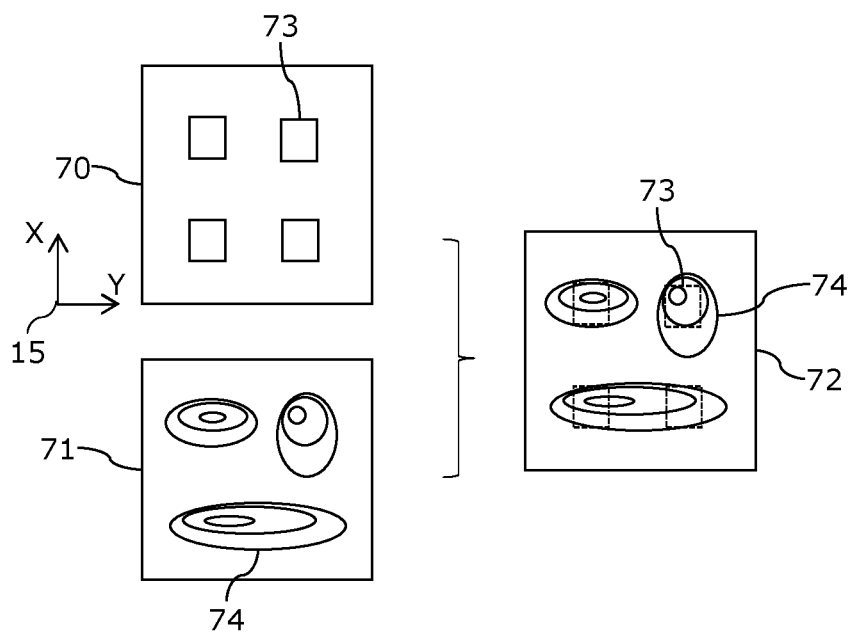
Fig. 6 ic # DEVICE AND METHOD FOR SURFACE PROFILOMETRY FOR THE CONTROL OF WAFERS DURING PROCESSING

BACKGROUND

The invention relates to a device for carrying out surface profilometry measurements on wafers during processing. It also relates to a measurement method implemented by the device.

The field of the invention is more particularly, but non-limitatively, that of the measurement and dimensional control of the devices in the field of microsystems (MEMS) and in microelectronics.

The manufacturing methods implemented in microelectronics generally rely on successive steps of the deposition of layers and etching, which result in the production of components in the form of stacks.

A very high degree of flatness of the layers is often necessary. Thus it is known to implement techniques, in particular optical profilometry, for measuring this flatness.

Among the optical profilometry techniques those called "full-field" are known which make it possible to obtain the shape of a surface directly in one or a small number of measurements. There are in particular interferometry techniques which use interferences between a measuring beam reflected by the surface to be measured and a reference beam. Different interferometer architectures are possible, some of which are known by the names Linnik, Mirau, Michelson or Fizeau interferometers.

Optical interferometry techniques are also known based on point-to-point distance measurements with a spot measuring beam which scans the surface. The detection techniques implemented in this case can in particular comprise the confocal, chromatic confocal techniques, or those based on interferometry or low-coherence interferometry (with broad-spectrum sources). They have the drawback however of being much slower than the full-field techniques.

A constraint common to all these techniques is that the reflectivity of the surface to be measured at the working wavelengths must be high in order to obtain good measurements. It is also necessary for the measurements not to be disturbed by stray reflections on the buried layers. Thus, wavelengths are generally used that do not penetrate into the materials, or only slightly (visible wavelengths for silicon), or, when the layers to be measured are transparent in the visible spectrum, metal deposition is carried out thereon beforehand (tantalum).

In certain situations, it is necessary to measure and characterize the flatness of layers that cover components or chips already produced, facing these components. The problem that then arises is that these components are not visible from the measurement face. It is thus difficult to attach or reference the flatness measurements to the exact position of these components, without using a priori design information which is inevitably inaccurate.

A purpose of the present invention is to propose a profilometry measurement device and method making it possible to carry out measurements of the shape of a surface that are registered or referenced accurately with respect to components buried in the wafer or at least located beneath the surface to be measured.

A purpose of the present invention is also to propose a profilometry measurement device and method making it possible to carry out measurements of the shape of a surface within a frame of reference linked to components buried in the wafer or at least located beneath the surface to be measured.

SUMMARY

This purpose is achieved with a device for carrying out measurements of shape on a first surface of a wafer relative to structures present beneath said first surface, characterized in that it comprises:
profilometry means arranged in order to carry out measurements of shape on said first surface of the wafer according to at least one measurement field;
imaging means facing said profilometry means and arranged in order to acquire a reference image of said structures on or through a second surface of the wafer opposite to the first surface according to at least one imaging field;
said profilometry means and said imaging means being arranged so that the measurement and imaging fields are referenced in position within a common frame of reference.

The structures can be for example components, tracks or chips which are buried in the layers of the wafer, or optionally produced on the face of the wafer opposite to the first surface. These are structures which are not visible on the first surface, and therefore which are beneath this surface from the point of view of the profilometry means.

The imaging means which face the profilometry means can be located in relation to a second surface, opposite to the first, of the wafer to be measured when the latter is positioned in the device of the invention. They make it possible to image the structures, or at least to obtain images which allow the structures to be located, even if these structures cannot be discerned through the first surface.

According to the invention, the profilometry means and the imaging means are spatially calibrated or referenced so that the position and the range of their respective measurement and imaging fields are each known with respect to the other, or in other words are referenced within one and the same frame of reference.

Preferably, the measurement and imaging fields can be represented in the shape of planes that are substantially parallel to each other. They can be referenced within a common frame of reference in the form of a reference plane.

Thus it is possible to attach or link the profilometry measurements to the position of the structures without the need for a priori knowledge of the exact position of the wafer in the device of the invention.

According to embodiments, the device according to the invention can comprise imaging means capable of producing images at wavelengths in the infrared.

Thus it is possible to image structures which are "buried" in the layers of the wafer, including through materials that are non-transparent in the visible wavelengths, such as silicon.

It is possible in particular to image structures through the substrate on which they are produced.

According to embodiments, the device according to the invention can comprise profilometry means using a full-field interferometer.

It can in particular comprise a full-field interferometer of one of the following types: Michelson, Mirau, Linnik, Fizeau.

Full-field interferometers are interferometers that make it possible to process measurement signals or two-dimensional interference structures representative of at least a portion of the surface to be measured.

According to embodiments, the profilometry means and the imaging means can have substantially parallel optical axes.

According to embodiments, the profilometry means and the imaging means can be aligned along a common optical axis.

According to embodiments, the device according to the invention can comprise profilometry means using a point distance sensor, and scanning means for scanning the first surface with said point distance sensor.

It can comprise in particular a distance sensor of one of the following types: confocal sensor, chromatic confocal sensor, interferometry, spectral-domain low coherence interferometer, time-domain low coherence interferometer, frequency-scanning low coherence interferometer, mechanical probe, atomic force microscopy (AFM) probe.

In this case, the height of the surface is measured from point to point, in order to reconstitute shape information.

The distance sensor can comprise any sensor capable of producing an item of information on the height or the local altitude of the surface. It may also involve in particular an optical sensor (confocal, interferometric), a mechanical sensor (probe), or a sensor that makes use of interactions at the atomic level between a probe point and the surface to be measured ("atomic force microscope" AFM).

The device according to the invention can also comprise a support for positioning a wafer with a first face facing profilometry means and a second face facing imaging means.

The wafer support can comprise a chuck.

According to another aspect, a method is proposed for carrying out measurements of shape on a first surface of a wafer relative to structures present beneath said first surface, which comprises the following steps:
  acquiring measurements of shape according to at least one measurement field on said first surface of the wafer by implementing profilometry means;
  acquiring a reference image of the structures according to at least one imaging field on or through a second surface of the wafer opposite to the first surface, implementing imaging means facing said profilometry means;
  said measurement and imaging fields are referenced in position within a common frame of reference.

According to embodiments, the method of the invention can also comprise a step of identification of the position of the structures in the reference image.

It can comprise a step of acquiring measurements of shape in proximity to at least one identified structure position.

According to embodiments, the method according to the invention can also comprise a prior step of calibration with location of the position of the measurement and imaging fields within a common frame of reference in the form of a reference plane.

BRIEF DESCRIPTIONS OF THE DRAWINGS

Other advantages and characteristics of the invention will become apparent on reading the detailed description of implementations and embodiments which are in no way limitative, and from the attached diagrams, in which:
  FIG. 1 shows an embodiment of the device according to the invention,
  FIG. 2 shows an embodiment of a profilometer with a full-field interferometer of the Michelson type,
  FIG. 3 shows an embodiment of a profilometer with a full-field interferometer of the Mirau type,
  FIG. 4 shows a first embodiment of the method according to the invention,
  FIG. 5 shows a second embodiment of the method according to the invention,
  FIG. 6 shows examples of measurements obtained with the device according to the invention.

DETAILED DESCRIPTION

It is well understood that the embodiments which will be described hereinafter are in no way limitative. Variants of the invention can be envisaged comprising only a selection of the characteristics described hereinafter, in isolation from the other characteristics described, if this selection of characteristics is sufficient to confer a technical advantage or to differentiate the invention with respect to the state of the art. This selection comprises at least one, preferably functional, characteristic without structural details, or with only a part of the structural details if this part alone is sufficient to confer a technical advantage or to differentiate the invention with respect to the state of the prior art.

In particular, all the variants and all the embodiments described can be combined together if there is no objection to this combination from a technical point of view.

In the figures, the elements common to several figures retain the same reference.

Firstly, with reference to FIG. 1, an embodiment of the device according to the invention will be described.

In a preferred embodiment, the device according to the invention is intended to carry out measurements of shape on a surface 13 of a wafer 12 which also comprises structures 14 in layers buried beneath the surface 13.

The device according to the invention then makes it possible to register or to represent within a common frame of reference 15 the measurements of the shape of the surface 13 and the structures 14 (or their position).

Thus, by way of non-limitative example, the device according to the invention can be used to monitor the flatness of a contact layer deposited over or in such a way as to cover structures 14 produced on the substrate of a wafer 12. These structures 14 can be in particular integrated circuits 14. In this case it is important to monitor the flatness of the contact layer accurately above the integrated circuits 14. Now, this contact layer does not allow visualization of the position of the integrated circuits on the side of the surface 13, in particular if it is covered with a metal layer.

It is thus possible with the device according to the invention to visualize and locate the integrated circuits 14 through the substrate which constitutes the portion of the wafer 12 opposite the surface 13 to be measured, and to carry out or register the measurements of shape with respect to the position of the integrated circuits 14.

The device according to the invention thus comprises profilometry means 10 which make it possible to carry out measurements of shape on the surface 13 of the wafer 12, when this wafer is positioned in a wafer support (not shown in FIG. 1).

The device according to the invention also comprises imaging means 11 intended to image the structures 14 present in or beneath the wafer 12 relative to the surface 13.

The profilometry means 10 and the imaging means 11 are arranged facing each other, on either side of the wafer 12 when the latter is positioned in the wafer support.

The wafer support is provided with means of movement and translation and/or rotation which make it possible to move and accurately position the wafer 12 with respect to the profilometry means 10 and imaging means 11.

A computer 28 controls the device and processes the data.

In the embodiment presented, the profilometry means 10 are in the form of a microscope with a full-field interferometer 20 at the level of the objective, which thus constitutes a full-field profilometer 10.

A light source 16, for example based on light-emitting diodes or a halogen source generates a light beam 19 in visible and/or near infrared wavelengths. This light beam 19 is directed towards the full-field interferometer 20 by a cube or a beamsplitter 18.

In the full-field interferometer 20, the light beam 19 is separated into a reference beam which illuminates a reference mirror and a measuring beam which illuminates the surface 13 of the wafer 12. The light reflected respectively by the surface 13 of the wafer and by the reference mirror is redirected to a matrix detector 17, for example of the CCD or CMOS type.

The profilometer 10 comprises optics and lenses, including an imaging objective, arranged so as to image the surface 13 of the wafer on the matrix detector 17. When the difference in optical paths between the measurement beam and the reference beam is less than the coherence length of the light source 16, interference fringes due to the interferences between the measurement beam and the reference beam are also visible. The demodulation of these interference fringes, according to techniques known to a person skilled in the art, makes it possible to reconstruct the shape of the surface 13 according to a measurement field corresponding substantially to the zone of this surface 13 imaged on the detector 17.

Different kinds of full-field interferometers 20 exist that can be used in the context of the invention.

With reference to FIG. 2, the full-field interferometer 20 can be in the Michelson configuration. It then comprises a separator cube 41 (or a beamsplitter) arranged between an imaging objective 40 and the surface 13 to be measured. This separator cube 41 reflects a fraction of the incident light beam 19 to a reference mirror 42 in order to generate the reference beam.

With reference to FIG. 3, the full-field interferometer 20 can also be in the Mirau configuration. It then comprises a semi-reflective beamsplitter 51 positioned between an imaging objective 40 and the surface 13 to be measured. This beamsplitter reflects a portion of the incident light to a reference mirror 52 positioned at the centre of the light beam.

The full-field interferometer can also be in a Linnik configuration. This configuration is a variant of the Michelson configuration in which an imaging objective is introduced into each arm of the interferometer. In this case, the separator cube 41 is located in front of the imaging objective in the light beam.

Of course, other configurations of full-field interferometers 20 are also possible within the context of the invention.

The profilometer also comprises translation means 43, for example by implementing a piezo-electric actuator, which makes it possible to move very accurately the assembly constituted by the interferometer 20 and the imaging objective 40 with respect to the surface to be measured 13. These translation means 43 make it possible to vary the optical path of the measurement beam between the separating element (for example the separator cube 41 in FIG. 2 or the beamsplitter 51 in FIG. 3) and the surface to be measured 13, without modifying the optical path of the reference beam between this separator element and the reference mirror. Thus it is possible to vary the phase of the interference structure obtained on the detector 17 in a known or controlled manner, and implement reconstruction algorithms of the "phase stepping" type which make it possible to reconstruct the shape of the surface 13 very accurately and unambiguously, on the basis of sequences of acquired images with different dephasing conditions.

The imaging means 11 are in the shape of an imaging microscope with a light source 23, an imaging objective 26, a matrix detector 27 (of the CCD or CMOS type for example) and a separator element 24 of the beamsplitter or separator cube type (for example).

The light 25 from the light source 23 is directed towards the rear face of the wafer by the separator element 24. The light reflected by the wafer 21 and collected by the imaging objective 26 is transmitted towards the matrix detector 27. The optical system with the imaging objective 26 is arranged so as to allow the formation of an image of the wafer on the matrix detector 22 according to an imaging field.

The light source 23 is designed so as to present an emission spectrum extending within the near infrared to reach wavelengths greater than 1 micrometer, for which silicon is no longer totally opaque. This light source 23 can be a halogen source. It is then possible, even with a matrix detector 22 based on silicon, to obtain an image of the structures 14 of the wafer 12 through a silicon layer such as the substrate.

As explained previously, the profilometry means 10 and the imaging means 11 are arranged so that the measurement and imaging fields are referenced in position within a common frame of reference 15.

To this end, the profilometry means 10 and the imaging means 11 are firmly fixed to a support which allows them to be held and/or positioned in a precise and stable manner in relation to each other.

They are moreover arranged so that the optical axis 21 of the profilometry means 10 and the optical axis 27 of the imaging means 11 substantially coincide, or at least are close and substantially parallel. In this way, the measurement and imaging fields are substantially superimposed at the level of the wafer 12, and the parallax errors due to the thickness of the wafer are avoided.

The device is then calibrated, for example by means of a sample or a calibration wafer 12 which comprises patterns on both faces, of which the positions of some in relation to the others are known. It should be noted that as the profilometer 10 is also an imaging system, the calibration can be carried out simply be imaging with a wafer 12 which comprises visible patterns on both faces.

Thus the measurement and imaging fields can be located within a common frame of reference 15 in two-dimensions (X-Y), or reference plane. In fact, it is not necessary to know the differences in height (relative to the thickness of the wafer 12) between the profilometry and imaging measurements, providing that care has been taken to position the optical axes 21, 27 of the profilometry and imaging means substantially parallel.

It is possible for example to attach the reference plane 15 to the imaging field which makes it possible to locate the structures 14 of the wafer, and calculate by calibration a transfer function in the plane (on the basis of translations, rotations and homothetic transformations) which makes it possible to locate the pixels of the measurement field within the imaging field.

The device of the invention makes it possible to acquire and process measurements in different ways.

By way of example, FIG. 4 shows a method for measuring surface shapes according to the invention which comprises:

a step of acquiring 60 a reference image with the imaging means 11:

a step of identifying 61 the position of the structures 14 of the wafer 12 (and optionally their shape) in the reference image, by implementing for example techniques for the segmentation of known images;

a step 62 of acquiring with the profilometer 10 the shape of the surface 13 of the wafer in one or more zone(s) corresponding to the position of the identified structures 14, taking account of the transfer function obtained during calibration.

Also by way of example, FIG. 5 shows a method for measuring a profile according to the invention which comprises:

a step of acquiring 60 a reference image 70 according to an imaging field with imaging means 11:

a step of identifying 61 the position of the structures 14 of the wafer 12 (and optionally their shape) in the reference image, by implementing for example techniques for the segmentation of known images;

a step 63 of acquiring the shape of the surface 13 of the wafer with the profilometer 10 in a measurement field superimposed at least partially on the imaging field used at the level of the wafer 12;

a step 64 of matching measurements of the shape and of the structures 14 by using the transfer function obtained during the calibration.

In this embodiment the step of identification 61 of the structures can be omitted if only a visual match is sought.

FIG. 6 illustrates the results of measurements that can be obtained with the invention, in particular in the implementation method described with respect to FIG. 5. It shows:

an image 70 obtained with the imaging means 11 with a representation 73 of the structures 14 of the wafer 12;

a representation 71 of the shape of the surface 13 of the wafer 12, obtained with the profilometry means 10 and in which the shape of the surface is represented in contour lines 74;

an image 72 combining the representation in contour lines 74 of the shape of the surface, after registration of the image 70 in the frame of reference 15, and the representations 73 of the structures 14.

Thus good visualisation of the defects of the flatnesses of the surface 13 of the wafer 12 with respect to the structures 14 is possible.

Of course, the invention is not limited to the examples which have just been described and numerous adjustments can be made to these examples without exceeding the scope of the invention.

The invention claimed is:

1. A device for carrying out measurements of shape on a first surface of a wafer relative to structures present beneath said first surface, comprising:

profilometry means arranged in order to carry out measurements of shape on said first surface of the wafer according to at least one measurement field;

imaging means facing said profilometry means and arranged in order to acquire a reference image of said structures on or through a second surface of the wafer opposite to the first surface according to at least one imaging field; and said profilometry means and said imaging means being arranged so that the measurement and imaging fields are referenced in position within a common frame of reference.

2. The device according to claim 1, comprising imaging means capable of producing images at wavelengths in the infrared.

3. The device according to claim 1, comprising profilometry means with a full-field interferometer.

4. The device according to claim 3, comprising a full-field interferometer of one of the following types: Michelson, Mirau, Linnik, or Fizeau.

5. The device according to claim 3, in which the profilometry means and the imaging means have substantially parallel optical axes.

6. The device according to claim 1, comprising profilometry means using a point distance sensor, and scanning means for scanning the first surface with said point distance sensor.

7. The device according to claim 6, comprising a distance sensor of the one of the following types: confocal sensor, chromatic confocal sensor, interferometry, spectral-domain low coherence interferometer, time-domain low coherence interferometer, frequency-scanning low coherence interferometer, mechanical probe, or atomic force microscopy (AFM) probe.

8. The device according to claim 1, also comprising a support for positioning a wafer with a first face facing said profilometry means and a second face facing said imaging means.

9. A method for carrying out measurements of shape on a first surface of a wafer relative to structures present beneath said first surface, comprising the following steps:

acquiring measurements of shape according to at least one measurement field on said first surface of the wafer by implementing profilometry means;

acquiring a reference image of the structures according to at least one imaging field on or through a second surface of the wafer opposite to the first surface, implementing imaging means facing said profilometry means; and said measurement and imaging fields are referenced in position within a common frame of reference.

10. The method according to claim 9, also comprising a step of identification of the position of the structures in the reference image.

11. The method according to claim 10, comprising a step of acquiring measurements of shape in proximity to at least one identified structure position.

12. The method according to claim 9, also comprising a prior step of calibration with location of the position of the measurement and imaging fields within a common frame of reference in the form of a reference plane.

* * * * *